United States Patent
Bazargan et al.

(10) Patent No.: US 11,207,463 B2
(45) Date of Patent: Dec. 28, 2021

(54) APPARATUSES, SYSTEMS, AND METHODS FOR IDENTIFYING AN INFUSATE IN A RESERVOIR OF AN INFUSION DEVICE

(71) Applicant: MEDTRONIC MINIMED, INC., Northridge, CA (US)

(72) Inventors: Afshin Bazargan, Simi Valley, CA (US); Sarnath Chattaraj, Simi Valley, CA (US); Hsi Chung Fusselman, Simi Valley, CA (US); Guangping Zhang, Calabasas, CA (US); Jinghua Chen, Encino, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 732 days.

(21) Appl. No.: 15/438,612

(22) Filed: Feb. 21, 2017

(65) Prior Publication Data
US 2018/0240236 A1     Aug. 23, 2018

(51) Int. Cl.
*A61M 5/172*     (2006.01)
*A61M 5/145*     (2006.01)
(Continued)

(52) U.S. Cl.
CPC ......... *A61M 5/1723* (2013.01); *A61M 5/145* (2013.01); *A61M 5/14248* (2013.01); *A61M 5/168* (2013.01); *A61M 2205/3306* (2013.01); *A61M 2205/3576* (2013.01); *A61M 2205/3584* (2013.01); *A61M 2205/3592* (2013.01); *A61M 2205/50* (2013.01); *A61M 2205/52* (2013.01);
(Continued)

(58) Field of Classification Search
CPC .................................................. A61M 5/1723
USPC ........................................................ 348/158
See application file for complete search history.

(56) References Cited

U.S. PATENT DOCUMENTS

| 3,631,847 A | 1/1972 | Hobbs, II |
| 4,212,738 A | 7/1980 | Henne |

(Continued)

FOREIGN PATENT DOCUMENTS

| DE | 4329229 | 3/1995 |
| EP | 0319268 | 11/1988 |

(Continued)

OTHER PUBLICATIONS (Animas Corporation, 1999). Animas . . . bringing new life to insulin therapy.

(Continued)

*Primary Examiner* — Daniel T Tekle
(74) *Attorney, Agent, or Firm* — Lorenz & Kopf, LLP

(57) ABSTRACT

Apparatuses and methods for identifying an infusate in a reservoir of an infusion device and systems for use in filling fluid delivery devices are provided. An exemplary apparatus for identifying an infusate in a reservoir of an infusion device includes a chamber in selective fluid communication with the reservoir. Further, the apparatus includes an indicator located in the chamber. The indicator exhibits a visual change when contacted by an infusate. The apparatus also includes a detector arrangement to identify the infusate by detecting the visual change in the indicator. An exemplary detector arrangement may include a camera to capture an image of the infusate and indicator in the chamber, and an identifier element to compare image data to a library of stored image data.

19 Claims, 7 Drawing Sheets

(51) Int. Cl.
*A61M 5/168* (2006.01)
*A61M 5/142* (2006.01)

(52) U.S. Cl.
CPC .............. *A61M 2205/6081* (2013.01); *A61M 2230/005* (2013.01); *A61M 2230/201* (2013.01)

(56) References Cited

U.S. PATENT DOCUMENTS

| | | |
|---|---|---|
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | Decant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,505,709 A | 4/1996 | Funderburk et al. |
| 5,497,772 A | 5/1996 | Schulman et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,259,937 B1 | 7/2001 | Schulman et al. |
| 6,329,161 B1 | 12/2001 | Keller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |

(56) References Cited

U.S. PATENT DOCUMENTS

| | | |
|---|---|---|
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,589,229 B1 | 7/2003 | Connelly et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,740,072 B2 | 5/2004 | Starkweather et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,817,990 B2 | 11/2004 | Yap et al. |
| 6,827,702 B2 | 12/2004 | Lebel et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,323,142 B2 | 1/2008 | Pendo et al. |
| 7,365,847 B2* | 4/2008 | Auton ............ G01N 27/44756 204/456 |
| 7,396,330 B2 | 7/2008 | Banet et al. |
| 7,402,153 B2 | 7/2008 | Steil et al. |
| 7,621,893 B2 | 11/2009 | Moberg et al. |
| 8,674,288 B2 | 3/2014 | Hanson et al. |
| 2001/0044731 A1 | 11/2001 | Coffman et al. |
| 2002/0013518 A1 | 1/2002 | West et al. |
| 2002/0022855 A1 | 2/2002 | Bobroff et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0193453 A1 | 9/2004 | Butterfield et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2008/0154503 A1 | 6/2008 | Wittenber et al. |
| 2009/0081951 A1 | 3/2009 | Erdmann et al. |
| 2009/0082635 A1 | 3/2009 | Baldus et al. |
| 2010/0121170 A1 | 5/2010 | Rule |
| 2011/0105952 A1* | 5/2011 | Bernstein ........... A61B 5/15105 600/573 |
| 2012/0184907 A1* | 7/2012 | Smith ............... A61M 5/14244 604/152 |
| 2012/0232362 A1 | 9/2012 | Gable et al. |
| 2014/0128960 A1* | 5/2014 | Greenslet ............. A61F 2/2415 623/1.15 |
| 2015/0314068 A1* | 11/2015 | Alderete, Jr. ...... A61M 5/14216 604/500 |
| 2016/0346456 A1* | 12/2016 | Cefai ....................... F03G 7/06 |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/3724 6 A1 | 11/1996 |
| WO | WO 96/36389 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | PCT/US02/03299 | 10/2002 |
| WO | WO 03/001329 | 1/2003 |
| WO | WO 03/094090 | 11/2003 |
| WO | WO 2005/065538 A2 | 7/2005 |

OTHER PUBLICATIONS

Bode B W, et al. (1996). Reduction in Severe Hypoglycemia with Long-Term Continuous Subcutaneous Insulin Infusion in Type I Diabetes. Diabetes Care, vol. 19, No. 4, 324-327.

Boland E (1998). Teens Pumping it Up! Insulin Pump Therapy Guide for Adolescents. 2nd Edition.

Brackenridge B P (1992). Carbohydrate Gram Counting A Key to Accurate Mealtime Boluses in Intensive Diabetes Therapy. Practical Diabetology, vol. 11, No. 2, pp. 22-28.

Brackenridge, B P et al. (1995). Counting Carbohydrates How to Zero in on Good Control. MiniMed Technologies Inc.

Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.

(56) References Cited

OTHER PUBLICATIONS

Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting A Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed•Technologies.
(Intensive Diabetes Management, 1995). Insulin Infusion Pump Therapy. pp. 66-78.
Disetronic My Choice™ D-TRON™ Insulin Pump Reference Manual. (Publication or release date no later than Nov. 2007).
Disetronic H-TRON® plus Quick Start Manual. (Publication or release date no later than Nov. 2007).
Disetronic My Choice H-TRONplus Insulin Pump Reference Manual. (Publication or release date no later than Nov. 2007).
Disetronic H-TRON® plus Reference Manual. (Publication or release date no later than Nov. 2007).
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(Minimed, 1997). MiniMed 507 Specifications. 2 pages. Retrieved on Sep. 16, 2003 from the World Wide Web: http://web.archive.org/web/19970124234841/www.minimed.com/files/mmn075.htm.
(Minimed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines/MiniMed™ Dosage Calculator Initial Basal Rate Guidelines Percentage Method. 4 pages.
(Minimed, 1996). MiniMed™ 507 Insulin Pump User's Guide.
(Minimed, 1997). MiniMed™ 507 Insulin Pump User's Guide.
(Minimed, 1998). MiniMed 507C Insulin Pump User's Guide.
(MiniMed International, 1998). MiniMed 507C Insulin Pump For those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(Minimed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.

Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263. (Publication or release date no later than Nov. 2007).
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Lineality," Sensors and Actuators, B. 10, 1992, pp. 37-40.
Kawamori, Ryuzo, et al., "Perfect Normalization of Excessive Glucagon Responses to Intravenous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.

(56) References Cited

OTHER PUBLICATIONS

Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.

Nakamoto, S., et al., "A Lift-Off Method for Patterning Enzyme-Immobilized Membranes in Multi-Biosensors," Sensors and Actuators 13, 1988, pp. 165-172.

Nishida, Kenro, et al., "Clinical applications of teh wearable artifical endocrine pancreas with the newly designed needle-type glucose sensor," Elsevier Sciences B.V., 1994, pp. 353-358.

Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.

Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.

Reach, G., "A Method for Evaluating in vivo the Functional Characteristics of Glucose Sensors," Biosensors 2, 1986, pp. 211-220.

Shaw, G. W., et al., "In vitro testing of a simply constructed, highly stable glucose sensor suitable for implantation in diabetic patients," Biosensors & Bioelectronics 6, 1991, pp. 401-406.

Shichiri, M., "A Needle-Type Glucose Sensor—A Valuable Tool Not Only For a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, el al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Neddle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri; Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G,, et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

\* cited by examiner

APPARATUSES, SYSTEMS, AND METHODS FOR IDENTIFYING AN INFUSATE IN A RESERVOIR OF AN INFUSION DEVICE

TECHNICAL FIELD

Embodiments of the subject matter described herein relate generally to medical devices, and more particularly, embodiments of the subject matter relate to the identification of fluids for delivery from infusion devices.

BACKGROUND

Infusion pump devices and systems are relatively well known in the medical arts, for use in delivering or dispensing a fluid agent or infusate, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics.

In practice, it is desirable to facilitate preparation of infusate for delivery to a patient or user. Specifically, there is a desire to reduce errors when preparing the infusate for delivery. Typically, a user must transfer the infusate from a vial to a device reservoir and then couple the device reservoir to a fluid delivery device. Different concentrations of infusates are increasingly common commercially. However, accidental use of a higher concentration than intended may cause severe injury or death to the patient.

Accordingly, there is a need to accurately identify the infusate in the reservoir before delivery from infusion devices. Further, there is a need to provide an automated apparatus, system and method for examining a fluid in the reservoir of an infusion device that satisfies the various requirements that may be imposed.

BRIEF SUMMARY

Apparatuses and methods for identifying an infusate in a reservoir of an infusion device and systems for use in filling fluid delivery devices are provided. An exemplary apparatus for identifying an infusate in a reservoir of an infusion device includes a chamber in selective fluid communication with the reservoir. Further, the apparatus includes an indicator located in the chamber. The indicator exhibits a visual change when contacted by a selected infusate. The apparatus also includes a detector arrangement to identify the infusate by detecting the visual change in the indicator. An exemplary detector arrangement may include a camera to capture an image of the infusate and indicator in the chamber, and an identifier element to compare image data to a library of stored image data.

In another embodiment, a system for use in filling a fluid delivery device includes a reservoir to hold a fluid and adapted for connection to the fluid delivery device. The system further includes a one-way valve interconnecting the reservoir and a chamber. The one-way valve selectively allows fluid flow from the reservoir to the chamber. Also, the system includes a camera to capture an image of the fluid in the chamber and to generate a signal including image data. Further, the system includes an identifier element in electronic communication with the camera to analyze the signal to identify the fluid.

Another embodiment provides a method for identifying an infusate in a reservoir of an infusion device. The method includes filling the reservoir with the infusate. A portion of the infusate flows through a one-way valve into a chamber and contacts an indicator located in the chamber. The indicator exhibits a visual change when contacted by the infusate. The method includes capturing an image of the infusate and indicator in the chamber. Also, the method includes generating a signal including data associated with the image. Further, the method includes analyzing the signal to identify the infusate.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
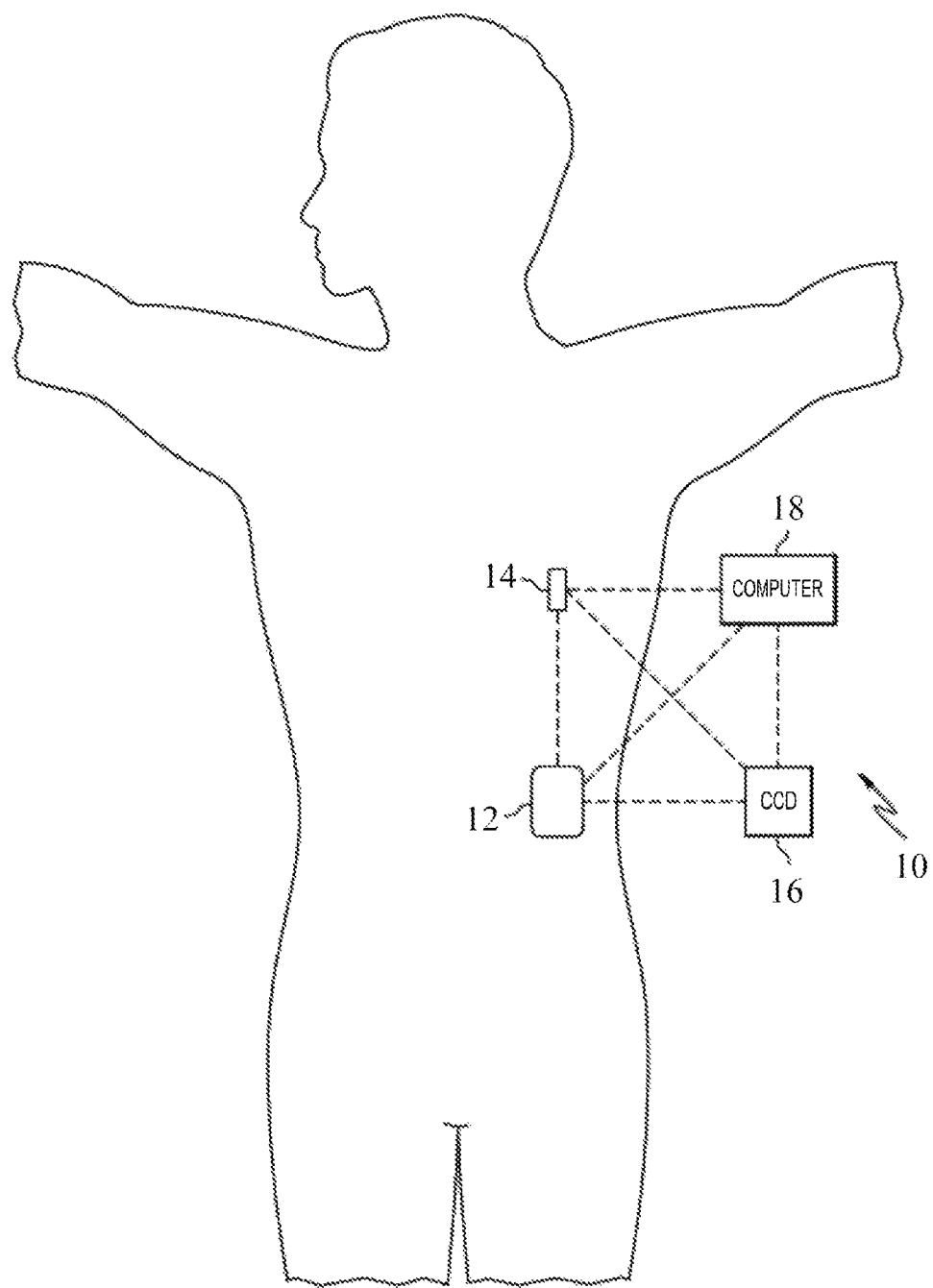
FIG. 1 depicts an infusion media delivery system for use by a patient in accordance with an embodiment herein.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

While the subject matter described herein can be implemented in any electronic device, exemplary embodiments described below are implemented in the form of medical devices, such as portable electronic medical devices. Although many different applications are possible, the following description focuses on a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Embodiments of the subject matter described herein generally relate to infusion systems including a fluid infusion device having an apparatus for identifying the infusate or infusion media that is prepared for delivery to the user or patient. Embodiments provide for automated examination of the infusate to ensure that the proper infusate and the proper concentration of the infusate are coupled to the fluid infusion device. Exemplary embodiments utilize an indicator that exhibits a visual change when contacted by a selected infusate. For example, the indicator may change color and may cause a portion of the infusate to change color. The resulting color is indicative of a specific infusate and concentration of the infusate. For example, a concentration of U-100, U-200, U-300, and U-500 insulins react differently to the indicator and form differently colored solutions.

In exemplary embodiments, a portion of the infusate is selectively separated from the reservoir and is contacted with the indicator. For example, a one-way valve may be utilized to transfer a portion of the infusate from the reservoir to a testing chamber. The one-way valve prevents flow of the indicator or of infusate mixed with the indicator from the testing chamber into the reservoir.

Exemplary embodiments further include an image capture device, such as a camera, for recording the color of the indicator and the portion of the infusate in the chamber. A signal including image data is then analyzed, such as by comparison with image data from previously tested infusates, to determine the identity of the infusate received in the reservoir.

The disclosure relates generally to delivery devices, systems and methods for delivering infusate or infusion media, such as a drug, to a recipient, such as a medical patient. In particular embodiments, a delivery device includes a disposable portion that secures to the recipient and that may be readily disposed of after it has been in use for a period of time. Such embodiments may be configured to provide a reliable, user-friendly mechanism to secure the delivery device to a patient for delivery of fluidic infusion media to the patient. Embodiments may be configured with feature that enhance the ease by which patients may secure the delivery device to the patient's skin and further features that enhance the ease by which patients may fill, re-fill or replace spent infusion media.

While embodiments are described herein with reference to an insulin delivery example for treating diabetes, other embodiments may be employed for delivering other infusion media to a patient for other purposes. For example, further embodiments may be employed for delivering other types of drugs to treat diseases or medical conditions other than diabetes, including, but not limited to drugs for treating pain or certain types of cancers, pulmonary disorders or HIV. Thus, the infusate may be insulin, HIV drugs, drugs to treat pulmonary hypertension, iron chelation drugs, pain medications, anti-cancer treatments, medications, vitamins, hormones, or the like. Further embodiments may be employed for delivering media other than drugs, including, but not limited to, nutritional media including nutritional supplements, dyes or other tracing media, saline or other hydration media, or the like.

A generalized representation of an infusion media delivery system 10 is shown in FIG. 1, wherein the system includes a delivery device 12 configured according to embodiments described herein. In the illustrated embodiment of FIG. 1, the infusion device 12 is designed as a portable medical device suitable for infusing an infusate, i.e., a fluid, a liquid, a gel, or other agent, into the body of a user.

The infusion media delivery system 10 may also include other components coupled for communication with the delivery device 12, including, but not limited to, a sensing arrangement 14 such as a sensor or monitor, a command control device (CCD) 16 and a computer 18. Each of the CCD 16, the computer 18 and the delivery device 12 may include receiver or transceiver electronics that allow communication with other components of the system. The delivery device 12 may include electronics and software for analyzing sensor data and for delivering infusion media according to sensed data and/or pre-programmed delivery routines. Some of the processing, delivery routine storage and control functions may be carried out by the CCD 16 and/or the computer 18, to allow the delivery device 12 to be made with more simplified electronics. However, in other embodiments, the infusion media delivery system 10 may comprise delivery device 12 without any one or more of the other components of the infusion media delivery system 10 shown in FIG. 1. The elements of the infusion system 10 may be similar to those described in U.S. Pat. No. 8,674,288, the subject matter of which is hereby incorporated by reference in its entirety.

In the generalized system diagram of FIG. 1, the delivery device 12 and sensor or monitor 14 are secured to a patient-user. The locations at which those components are secured to the patient-user in FIG. 1 are provided only as a representative, non-limiting example. The delivery device 12 and sensor or monitor 14 may be secured at other locations on the patient, and such locations may depend upon the type of treatment to be administered by the infusion media delivery system 10. As described in further detail below, the delivery device 12 contains a reservoir of infusate or infusion media and delivers the infusate into the patient's body in a controlled manner.

The sensing arrangement 14 generally represents the components of the fluid delivery or infusion system 10 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 14 may include electronics and enzymes reactive to a biological or physiological condition of the user, such as a blood glucose level, or the like, and provide data indicative of the blood glucose level to the infusion device 12, the CCD 16 and/or the computer 18. For example, the infusion device 12, the CCD 16 and/or the computer 18 may include a display for presenting information or data to the user based on the sensor data received from the sensing arrangement 14, such as, for example, a current glucose level of the user, a graph or chart of the user's glucose level versus time, device status indicators, alert messages, or the like. In other embodiments, the infusion device 12, the CCD 16 and/or the computer 18 may include electronics and software that are configured to analyze sensor data and operate the infusion device 12 to deliver fluid to the body of the user based on the sensor data and/or preprogrammed delivery routines. Thus, in exemplary embodiments, one or more of the infusion device 12, the sensing arrangement 14, the CCD 16, and/or the computer 18 includes a transmitter, a receiver, and/or other transceiver electronics that allow for communication with other components of the infusion system 10, so that the sensing arrangement 14 may transmit sensor data or monitor data to one or more of the infusion device 12, the CCD 16 and/or the computer 18.

Still referring to FIG. 1, in various embodiments, the sensing arrangement 14 may be secured to the body of the user or embedded in the body of the user at a location that is remote from the location at which the infusion device 12 is secured to the body of the user. In various other embodiments, the sensing arrangement 14 may be incorporated within the infusion device 12. In other embodiments, the sensing arrangement 14 may be separate and apart from the infusion device 12, and may be, for example, part of the CCD 16. In such embodiments, the sensing arrangement 14 may be configured to receive a biological sample, analyte, or the like, to measure a condition of the user.

In various embodiments, the CCD 16 and/or the computer 18 may include electronics and other components configured to perform processing, delivery routine storage, and to control the infusion device 12 in a manner that is influenced by sensor data measured by and/or received from the sensing arrangement 14. By including control functions in the CCD 16 and/or the computer 18, the infusion device 12 may be made with more simplified electronics. However, in other embodiments, the infusion device 12 may include all control functions, and may operate without the CCD 16 and/or the computer 18. In various embodiments, the CCD 16 may be a portable electronic device. In addition, in various embodiments, the infusion device 12 and/or the sensing arrangement 14 may be configured to transmit data to the CCD 16 and/or the computer 18 for display or processing of the data by the CCD 16 and/or the computer 18.

In some embodiments, the CCD 16 and/or the computer 18 may provide information to the user that facilitates the user's subsequent use of the infusion device 12. For example, the CCD 16 may provide information to the user to allow the user to determine the rate or dose of medication to be administered into the user's body. In other embodiments, the CCD 16 may provide information to the infusion device 12 to autonomously control the rate or dose of medication administered into the body of the user. In some embodiments, the sensing arrangement 14 may be integrated into the CCD 16. Such embodiments may allow the user to monitor a condition by providing, for example, a sample of his or her blood to the sensing arrangement 14 to assess his or her condition. In some embodiments, the sensing arrangement 14 and the CCD 16 may be used for determining glucose levels in the blood and/or body fluids of the user without the use of, or necessity of, a wire or cable connection between the infusion device 12 and the sensing arrangement 14 and/or the CCD 16.

In one or more exemplary embodiments, the sensing arrangement 14 and/or the infusion device 12 are cooperatively configured to utilize a closed-loop system for delivering fluid to the user. Examples of sensing devices and/or infusion pumps utilizing closed-loop systems may be found at, but not limited to, the following U.S. Pat. Nos. 6,088,608, 6,119,028, 6,589,229, 6,740,072, 6,827,702, 7,323,142, and 7,402,153, all of which are incorporated herein by reference in their entirety. In such embodiments, the sensing arrangement 14 is configured to sense or measure a condition of the user, such as, blood glucose level or the like. The infusion device 12 is configured to deliver fluid in response to the condition sensed by the sensing arrangement 14. In turn, the sensing arrangement 14 continues to sense or otherwise quantify a current condition of the user, thereby allowing the infusion device 12 to deliver fluid continuously in response to the condition currently (or most recently) sensed by the sensing arrangement 14 indefinitely. In some embodiments, the sensing arrangement 14 and/or the infusion device 12 may be configured to utilize the closed-loop system only for a portion of the day, for example only when the user is asleep or awake.

Figure 2:
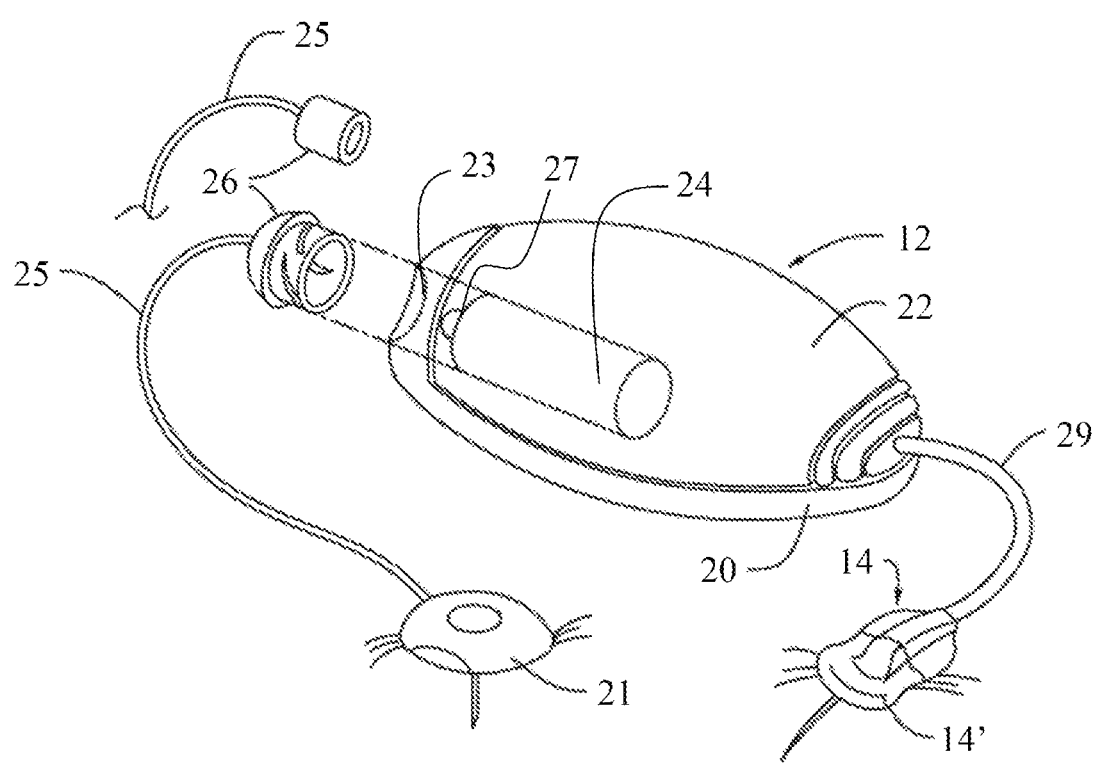
FIG. 2 depicts a plan view of an exemplary embodiment of a fluid infusion device suitable for use in the infusion system of FIG. 1.

An example of a patch-like delivery device 12 according to an embodiment is shown in FIG. 2. The delivery device 12 in FIG. 2 includes a disposable base portion 20 and a durable portion 22. The disposable base portion 20 may include structural elements that ordinarily contact the patient's skin or infusion media, during operation of the delivery device 12. On the other hand, the durable portion 22 may have elements (including electronics, motor components, linkage components, and the like) that do not ordinarily contact the patient or infusion media during operation of the delivery device 12. Thus, elements in the durable portion 22 of the delivery device 12 are typically not contaminated from contact with the patient or infusion media during normal operation of the delivery device 12.

In the illustrated embodiment, the disposable portion of the delivery device 12 comprises a disposable base portion 20 that supports a reservoir 24. The durable portion 22 may comprise a housing that secures onto the base portion 20 and covers the reservoir 24. The durable portion 22 may house a suitable drive device, such as an electrically operated motor (not shown in FIG. 2), and drive linkage components (not shown in FIG. 2) for driving fluid out of the reservoir 24. The durable portion 22 also may house suitable control electronics (not shown in FIG. 2) for controlling the operation of the drive device to drive fluid from the reservoir 24 in a controlled manner. Further embodiments may include communication electronics (not shown in FIG. 2) within the durable portion 22, for communicating with the sensor or monitor 14, the CCD 16, the computer 18 and/or other components of the infusion media delivery system 10.

The disposable base portion 20 has a bottom surface (facing downward and into the page in FIG. 2) that is configured to secure to a patient's skin at a desired location on the patient. A suitable adhesive may be employed at the interface between the bottom surface of the base portion 20 and the patient's skin, to adhere the base portion 20 to the patient's skin. The adhesive may be provided on the bottom surface of the base portion 20, with a removable cover layer covering the adhesive material. In this manner, a patient-user may peel off the cover layer to expose the adhesive material and then place the adhesive side of the base portion 20 against the patient's skin.

The base portion 20 may include a suitable opening or port 23 for connecting a hollow tube 25 to the reservoir 24, to convey infusion media from the reservoir 24. One end of the tube 25 may have a suitable connector 26, such as, but not limited to a Luer connector or a threaded cap connector having a hollow needle for coupling (in fluid-flow communication) to a corresponding connector 27 on the reservoir 24. Alternatively or in addition, the reservoir 24 may include a septum as part of the connector 27, for receiving an end of a hollow needle. The opening or port on the base portion 20 may be provided with corresponding connector structure, such as, but not limited to a Luer connector receptacle or a threaded receptacle shaped to receive a threaded cap connector. Other embodiments may employ other suitable connectors or connection arrangements for connecting one end of the tube 25 in fluid-flow communication with the reservoir 24.

The other end of the tube 25 may connected to a hollow needle 21 for piercing the patient's skin and conveying infusion media into the patient. The hollow needle 21 may be secured to the patient's skin, for example, by manual application or with the assistance of an insertion tool, such as, but not limited to the insertion tool described in U.S. Patent Application Publication No. 2002/0022855, titled "Insertion Device For An Insertion Set And Method Of Using The Same." In other embodiments, as described below, a hollow needle and insertion mechanism may be included within the delivery device 12, so as to avoid the need for a port 23, tube 25 and connector 26.

The durable portion 22 of the delivery device 12 includes a housing shell configured to mate with and secure to the disposable base portion 20. The durable portion 22 and base portion 20 may be provided with correspondingly shaped grooves, notches, tabs or other suitable features that allow the two parts to easily snap together, by manually pressing the two portions together in a manner well known in the mechanical arts. In a similar manner, the durable portion 22 and base portion 20 may be separated from each other by manually applying sufficient force to unsnap the two parts from each other. In further embodiments, a suitable seal, such as an o-ring seal, may be placed along the peripheral edge of the base portion 20 and/or the durable portion 22, so as to provide a seal against water between the base portion 20 and the durable portion 22.

The durable portion 22 and base portion 20 may be made of suitably rigid materials that maintain their shape, yet provide sufficient flexibility and resilience to effectively snap together and apart, as described above. The base portion 20 material may be selected for suitable compatibility with the patient's skin. For example, the base portion 20 and the durable portion 22 of the delivery device 12 may be made of any suitable plastic, metal, composite material or the like. The base portion 20 may be made of the same type of material or a different material relative to the durable portion 22. The base portion and durable portions may be manufactured by injection molding or other molding processes, machining processes or combinations thereof.

For example, the base portion 20 may be made of a relatively flexible material, such as a flexible silicon, plastic, rubber, synthetic rubber or the like. By forming the base portion of a material capable of flexing with the patient's skin, a greater level of patient comfort may be achieved when the base portion is secured to the patient's skin. Also, a flexible base portion 20 can result in an increase in the site options on the patient's body at which the base portion 20 may be secured.

In the embodiment illustrated in FIG. 2, the durable portion 22 of the delivery device 12 is connected to sensor 14, through a sensor lead 29. Sensor 14 may comprise any suitable biological or environmental sensing device, depending upon the nature of the treatment to be administered by the delivery device 12. For example, in the context of delivering insulin to a diabetes patient, the sensor 14 may comprise a blood glucose sensor.

The sensor 14 may be an external sensor that secures to the patient's skin or, in other embodiments, may be an implantable sensor that is located in an implant site within the patient. In the illustrated example of FIG. 2, the sensor 14 is an external sensor having a disposable needle pad 14' that includes a needle for piercing the patient's skin and enzymes and/or electronics reactive to a biological condition, such as blood glucose level, of the patient. The disposable needle pad 14' may electrically contact electrical conductors in the lead 29, to convey electrical signals from the sensor 14 to suitable sensor electronics located within the durable portion 22 of the delivery device 12. The lead 29 may have any suitable length. In this manner, the delivery device 12 may be provided with sensor data from a sensor secured to the patient, at a site remote from the location at which the delivery device 12 is secured to the patient.

While the embodiment shown in FIG. 2 includes a sensor 14 connected by a lead 29 for providing sensor data to sensor electronics located within the durable portion 22 of the delivery device 12, other embodiments may employ a sensor 14 located within the delivery device 12. Yet other embodiments may employ a sensor 14 having a transmitter for communicating sensor data by a wireless communication link with to receiver electronics located within the durable portion 22 of the delivery device 12. The wireless connection between the sensor 14 and the receiver electronics in the durable portion 22 of the delivery device 12 may comprise a radio frequency RF connection, an optical connection, or another wireless suitable communication link. Further embodiments need not employ a sensor and, instead, provide infusion media delivery functions without the use of sensor data.

As described above, by separating disposable elements of the delivery device 12 from durable elements, the disposable elements may be arranged on the disposable base portion 20, while durable elements may be arranged within a separable durable portion 22. In this regard, after one (or a prescribed number) of uses of the delivery device 12, the disposable base portion 20 may be separated from the durable portion 22, so that the disposable base portion 20 may be disposed of in a proper manner. The durable portion 22 may, then, be mated with a new (un-used) disposable base portion 20 for further delivery operation with a patient.

The reservoir 24 may be supported by the disposable base portion 20 in any suitable manner. The reservoir 24 may be provided as a cartridge or generally cylindrical canister for containing fluidic infusion media. For example, the base portion 20 may be provided with projections or struts, or a trough feature for holding a cartridge-type reservoir in a manner that allows a user to readily remove the reservoir from the base portion and re-install a new or refilled reservoir, when replacement or re-filling is needed, as described with respect to further embodiments below. Alternatively, or in addition, the reservoir 24 may be secured to the base portion 20 by a suitable adhesive or other coupling structure. The reservoir 24 has a port and may be supported by the base portion 20 in a position at which a connector 26 may engage or otherwise come into fluid flow communication with the reservoir port, when the connector 26 is connected to the port 23 on the base portion 20.

The durable portion 22 of the delivery device 12 may include a motor or other force-applying mechanism, for applying a force to the infusion media within the reservoir 24 to force fluidic infusion media out of the reservoir 24 and into the needle 27, for delivery to the patient. For example, an electrically driven motor may be mounted within the durable portion 22 with appropriate linkage for causing the motor to operably engage a piston of the reservoir and drive the reservoir piston in a direction to cause the fluidic pressure within the reservoir 24 to increase and thereby force fluidic infusion media out of the reservoir port, into the tube 25 and needle 27. The motor may be arranged within the durable portion 22 and the reservoir may be correspondingly arranged on the disposable base portion 20, such that the operable engagement of the motor with the reservoir piston (e.g., through appropriate linkage) occurs automatically upon the patient-user snap fitting the durable portion 22 onto the disposable base portion 20 of the delivery device 12.

Figure 3:
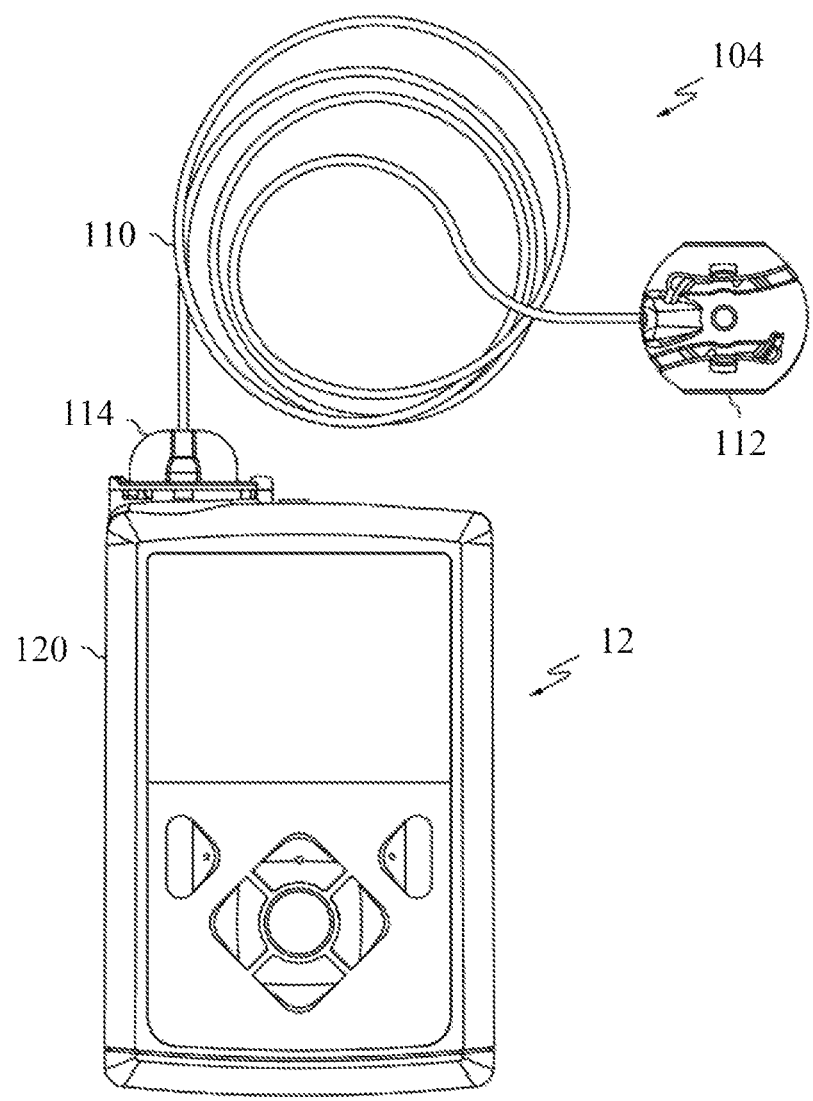
FIG. 3 depicts a plan view of an exemplary embodiment of another fluid infusion device suitable for use in the infusion system of FIG. 1.

While FIG. 2 illustrates an embodiment of a patch-like delivery device 12 for use in the fluid delivery system 10, FIG. 3 illustrates an exemplary embodiment of a fluid infusion delivery device 12 coupled with an infusion set 104 with a fluid conduit assembly for use in the fluid delivery system 10 of FIG. 1. The fluid infusion delivery device 12 accommodates a fluid reservoir (hidden from view in FIG. 3) for the infusate to be delivered to the user.

The illustrated embodiment of the infusion set 104 includes, without limitation: a length of tubing 110; an infusion unit 112 coupled to the distal end of the tubing 110; and a connector 114 coupled to the proximal end of the tubing 110. The fluid infusion delivery device 12 is designed to be carried or worn by the patient, and the infusion set 104 terminates at the infusion unit 112 such that the fluid infusion delivery device 12 can deliver fluid to the body of the patient via the tubing 110. The infusion unit 112 includes a cannula (hidden from view in FIG. 3) that is coupled to the distal end of the tubing 110. The cannula is inserted into the skin and is held in place during use of the fluid infusion delivery device 12.

The infusion set 104 defines a fluid flow path that fluidly couples a fluid reservoir to the infusion unit 112. The connector 114 mates with and couples to a section of the fluid reservoir (not shown), which in turn is coupled to a housing 120 of the fluid infusion delivery device 12. The connector 114 establishes the fluid path from the fluid reservoir to the tubing 110. Actuation of the fluid infusion delivery device 12 causes the medication fluid to be expelled from the fluid reservoir, through the infusion set 104, and into the body of the patient via the infusion unit 112 and cannula at the distal end of the tubing 110. Accordingly, when the connector 114 is installed as depicted in FIG. 3, the tubing 110 extends from the fluid infusion delivery device 12 to the infusion unit 112, which in turn provides a fluid pathway to the body of the patient.

The fluid infusion delivery device 12 includes a radio frequency (RF) antenna to support wireless data communication with other devices, systems, and/or components. The RF antenna can be located inside the housing 120 or it can be integrally formed with the housing 120. Accordingly, the RF antenna is hidden from view in FIG. 3.

Figure 4:
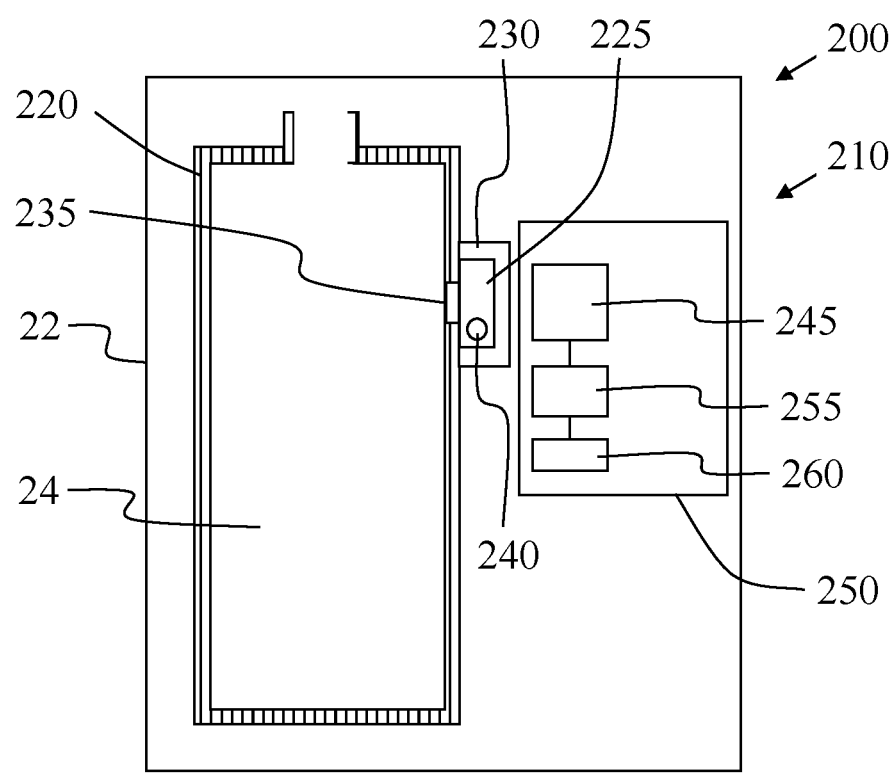
FIG. 4 depicts a plan view of an exemplary embodiment of an apparatus for identifying a fluid in the reservoir of the fluid infusion device of FIG. 2 or 3.

As may be understood from FIGS. 1-3, each embodiment of the fluid delivery device 12 includes a reservoir for holding an infusate and a fluid path for delivering the infusate from the reservoir to the patient. FIG. 4 illustrates an embodiment of an apparatus and system for identifying the infusate in the reservoir.

In FIG. 4, an identifying system 200 is provided for use with the fluid delivery device of FIGS. 1-3. The identifying system 200 includes a detector arrangement 210 to identify the infusate by detecting a visual change in the indicator.

As shown, a fluid reservoir 24 is received by a portion 22 of the delivery device. The reservoir 24 is bounded by a wall 220. Also, a testing chamber 225 is provided in the identifying system 200. The testing chamber 225 is bound by a wall 230. In an exemplary embodiment, at least a portion of the wall 230 is transparent. For example, the wall 230 may be formed from a transparent material such as clear polycarbonate, polypropylene, polyurethane/polypropylene, or other clear polymeric material. Alternatively or additionally, the wall 230 may be formed with a transparent window formed from clear polycarbonate, polypropylene, polyurethane/polypropylene, or other clear polymeric material. In certain embodiments, the wall 220 of the reservoir 24 and the wall 230 of the testing chamber 225 are integrally formed. In other words, the testing chamber 225 in certain embodiments is realized as an extension or a pocket of the reservoir 24.

As shown, the reservoir 24 and testing chamber 225 are selectively coupled by a one-way valve that allows for selective fluid flow from the reservoir 24 to the testing chamber 225 and which prevents back flow from the testing chamber 225 to the reservoir 24. Suitable one-way valves may include ball check valves, diaphragm check valves, swing/tilting check valves, stop-check valves, lift-check valves, in-line check valves, duckbill valves, pneumatic non-return valves, or others.

In the illustrated embodiment, an indicator 240 is located in the testing chamber 225. In an exemplary embodiment, the indicator is an indicator chemical, such as dithizone, pseudoisocyanin compounds, aldehyde fuchsin, Victoria 4R blue, various chromophore/fluorophore labelled insulin antibodies, and others. In other embodiments, the indicator 240 can be a small piece of carrier material having an indicator chemical applied to it and/or having an indicator chemical impregnated therein. In yet other embodiments, the indicator 240 can be realized as or attached to an inner surface of the chamber 225. The indicator 240 may be provided in solid or fluid phase. During manufacture of the reservoir 24 and testing chamber 225, the indicator 240 is sealed in the testing chamber 225 by the one-way valve.

An exemplary indicator 240 exhibits and/or causes the infusate to exhibit a visual change when the indicator 240 is contacted by the infusate. For example, the indicator 240 may exhibit and/or cause the infusate to exhibit a color change when the indicator 240 is contacted by the infusate. In exemplary embodiments, the indicator causes a change to a first color when contacted with a first infusate, such as U-100 insulin, a change to a second color when contacted with a second infusate, such as U-200 insulin, a change to a third color when contacted with a third infusate, such as U-300 insulin, or a change to a fourth color when contacted with a fourth infusate, such as U-500 insulin. For example, if the concentration of the indicator (e.g. dithizone, a light blue color) is fixed, the color developed by mixing the indicator with insulin at various concentrations may vary from light pink to dark pink. If measured at a wavelength of 530 nm, the absorbance will be linear to insulin concentration for a properly designed test system. If the indicator is mixed with other non-insulin formulations, the resulting color will not be pink.

In FIG. 4, the detector arrangement 210 is shown to include a receiver element 245 for receiving light from the testing chamber 225. The receiver element 245 may be aligned with a window in the wall 230, if provided. An exemplary receiver element 245 is a camera, a color sensitive light sensor, or a photosensor (such as a charge coupled device array as commonly found in digital cameras). An exemplary camera 245 is configured to capture images of the fluid and indicator 240 in the testing chamber 225. Further, the exemplary camera 245 generates a signal, such as a signal including image data. For example, the exemplary camera 245 may generate a digital file of the image.

As shown, the detector arrangement 210 further includes a printed circuit board (PCB) 250. The receiver element 245 is coupled to the PCB 250. The PCB 250 may be part of receiver electronics. The PCB 250 may be in communication with sensing arrangement 14, CCD 16 or computer 18 of FIG. 1 through the receiver electronics.

In FIG. 4, the detector arrangement 210 further includes an identifier element 255 electronically connected to the receiver element 245. The identifier element 255 may receive and analyze the signal from the receiver element 245. Alternatively, the sensing arrangement 14, CCD 16 or computer 18 may include an identifier element for analyzing the signal from the receiver element 245.

In an exemplary embodiment, the identifier element 255 analyses the signal received from the receiver element 245 by comparing the image data therein with image data from a library of previously tested infusates and their associated image data. For this reason, the identifier element 255 may include or be in electronic communication with a memory storage or library 260 storing the image data of known infusates and concentrations of infusates.

As shown, the receiver element 245, identifier element 255 and memory storage 260 are coupled to the PCB 250 such that the PCB 250 may activate and identification operation. For example, the PCB 250 may active an identification operation when the reservoir is filled, when the user prompts the delivery device, or during preset time intervals. Further, through communication with the sensing arrangement 14, CCD 16 or computer 18, the PCB 250 may verify that the identified infusate is the proper infusate, i.e., the expected infusate. Alternatively, if the identified infusate is different from the expected infusate, the PCB 250 may communicate the identity of the infusate and the infusate concentration to the sensing arrangement 14, CCD 16 or computer 18 so that a fluid delivery regime may be modified for use with the identified infusate.

Figure 5:
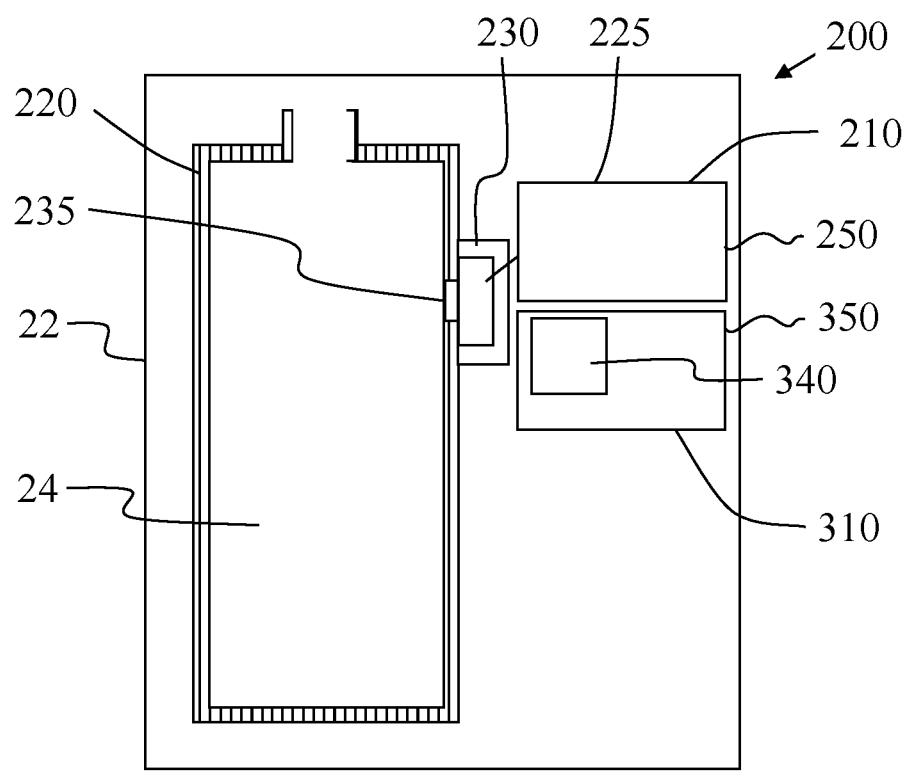
FIG. 5 depicts a plan view of another exemplary embodiment of an apparatus for identifying a fluid in the reservoir of the fluid infusion device of FIG. 2 or 3.

FIG. 5 illustrates an embodiment in which the identifying apparatus 200 includes more than one detector arrangement. As shown, the identifying apparatus 200 includes a detector arrangement 210 and the elements thereof as described in relation to FIG. 4. Also, the identifying apparatus 200 includes a detector arrangement 310 that performs orthogonal identification.

The detector arrangement 310 includes a transceiver 340 provided with both a transmitter element and a receiver element. The transceiver 340 may be aligned with a window in the wall 230, if provided, so that the transceiver 340 may transmit a beam of energy through the window, or through a transparent or translucent portion of wall 230, and into contact with an infusate located in the testing chamber 225, and may receive a reflected beam of energy from the infusate back to the transceiver 340.

As further shown, the transceiver 340 is mounted to a printed circuit board (PCB) 350 that may be part of receiver electronics located within the durable portion 22. The PCB 350 may be an additional PCB, or may be part of PCB 250. The PCB 350 may be in communication with sensing arrangement 14, CCD 16 or computer 18 of FIG. 1 through the receiver electronics. The PCB 350 may serve as an identifier element for analyzing a signal received by a receiver element of the transceiver 340. Alternatively, the sensing arrangement 14, CCD 16 or computer 18 may include an identifier element for analyzing a signal received by a receiver element of the transceiver 340. In either case, the identifier element may analyze an electronic representation of the signal that may include electric or intensity readings at one or more wavelengths or a spectra over an selected range of wavelengths, such as from 0.2 to 16 µm.

While FIG. 5 illustrates an embodiment in which the detector arrangement 310 includes a transceiver 340 that is mounted to a durable portion 22, other embodiments are contemplated. For example, the transmitter element and receiver element of the transceiver 340 may be physically decoupled from the conduit where analysis is to be performed. Also, the transmitter and receiver elements of the transceiver 340 may be mounted to the wall 230 of the conduit where analysis is to be performed. Further, transmitter and receiver elements of the transceiver 340 may be located within the conduit where analysis is to be performed. Also, transmitter and receiver elements of the transceiver 340 could be formed as parts of other components within the fluid delivery device.

As contemplated herein, the detector arrangement 310, including transmitter and receiver elements of the transceiver 340, may be located in any suitable location along the fluid path of a fluid delivery device 12. For example, the detector arrangement 310 could be provided to transmit a beam of energy into contact with an infusate located in the reservoir 24 and to receive a reflected beam of energy from the infusate back to the transceiver 340. As used herein, any of the components containing or delivering a flow of an infusate are considered a conduit where a detector arrangement 310 may be located.

Further, a fluid delivery device 12 may be provided with more than one detector arrangements 310 and/or more than one detector arrangements 210. In an exemplary embodiment, each of the detector arrangements 310 transmits a beam of energy into the fluid orthogonally to the direction of fluid flow or to the wall of the vessel through which the fluid flows.

Detector arrangements 310 may identify the composition and concentration of a fluid or infusate within a conduit, such as a reservoir, hollow tube, or other fluid path, that is bound by a wall. In certain embodiments, the wall may be transparent and not include a separate distinct window. In embodiments, a beam of energy, such as IR, NIR, or UV energy, is transmitted into the conduit from a transmitter element of the transceiver 340 and interacts with the infusate and any foreign matter therein. For example, different portions or wavelength ranges of the beam of energy may be absorbed, refracted or reflected. In certain embodiments, a resulting beam of energy passes out of the conduit and is received by a receiver element of the transceiver 340 as a signal. The signal can be analyzed to determine the composition and concentration of the infusate and whether foreign matter is present in the infusate.

Figure 6:
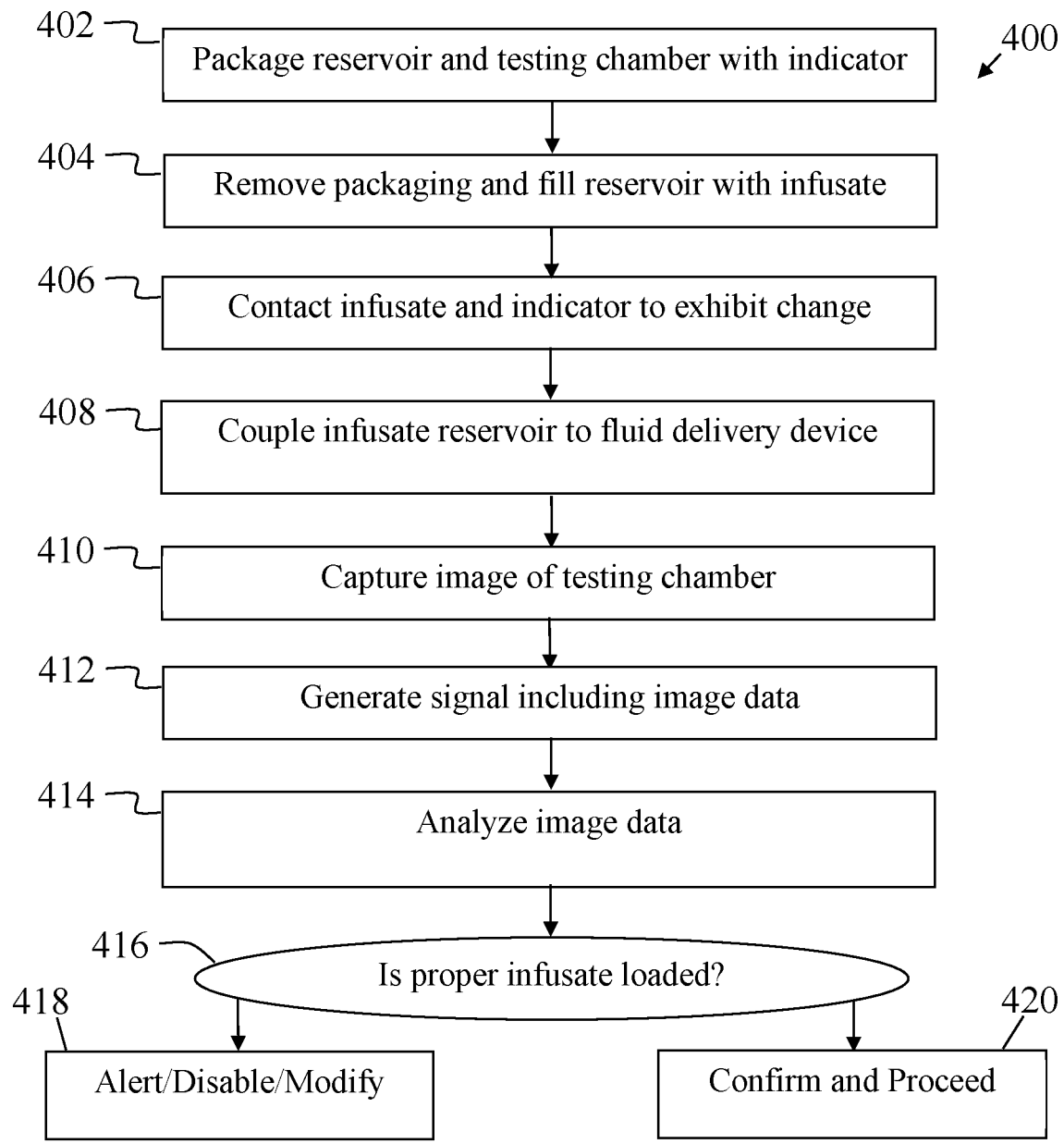
FIG. 6 is a flow chart illustrating a method for identifying a fluid for delivery in accordance with an embodiment.

FIG. 6 illustrates an exemplary method 400 for identifying a fluid for delivery to a body of a user. As shown, an initial manufacturing step 402 provides for packaging the reservoir 24 and testing chamber 225 with the indicator 240. In exemplary embodiments, the indicator 240 is sealed in the testing chamber 225 by the one-way valve 235. Thus, a manufacturing process may form and package the compound bundled reservoir 24 and testing chamber 225 with the indicator 240. Therefore, a user may remove the bundled reservoir 24 and testing chamber 225 from packaging and fill the reservoir with the desired infusate for infusion from a delivery device such as at step 404.

Upon filling the reservoir 24 with infusate, the one-way valve permits a portion of the infusate to enter the testing chamber 225 and contact the indicator. Upon contact therebetween, a visual change such as a color change is exhibited, such as at step 406.

Then, the user may couple the infusate reservoir with the fluid delivery device at step 408. Upon coupling, the identification process may be automatically initiated to confirm that the correct infusate is loaded in the fluid delivery device.

Alternatively, the identification process may be initiated by the user or during preset time intervals. In either case, the identification process includes capturing an image of the testing chamber including the indicator and infusate, or a solution thereof, at step 410. Further, the method 400 includes generating a signal including image data at step 412. The signal may be generated by the receiver element or camera and then communicated to the identifier element.

At step 414, the method analyzes the image data, such as by comparing the image data with stored image data associated with known infusates at known concentrations. In this manner, the identity of the infusate and concentration of the infusate received in the reservoir can be identified.

At step 416, the method queries whether, based on the image data comparison, the proper or expected infusate is loaded in the fluid delivery device. If not, the PCB, sensing arrangement, CCD or computer may automatically alert the user and/or disable infusion of the infusate from the fluid delivery device or modify fluid delivery to an appropriate process for the identified infusate at step 418. On the other hand, if the correct infusate is loaded, the PCB, sensing arrangement, CCD or computer may confirm that the correct infusate is loaded and allow the fluid delivery device to proceed with an infusion process at step 420.

Figure 7:
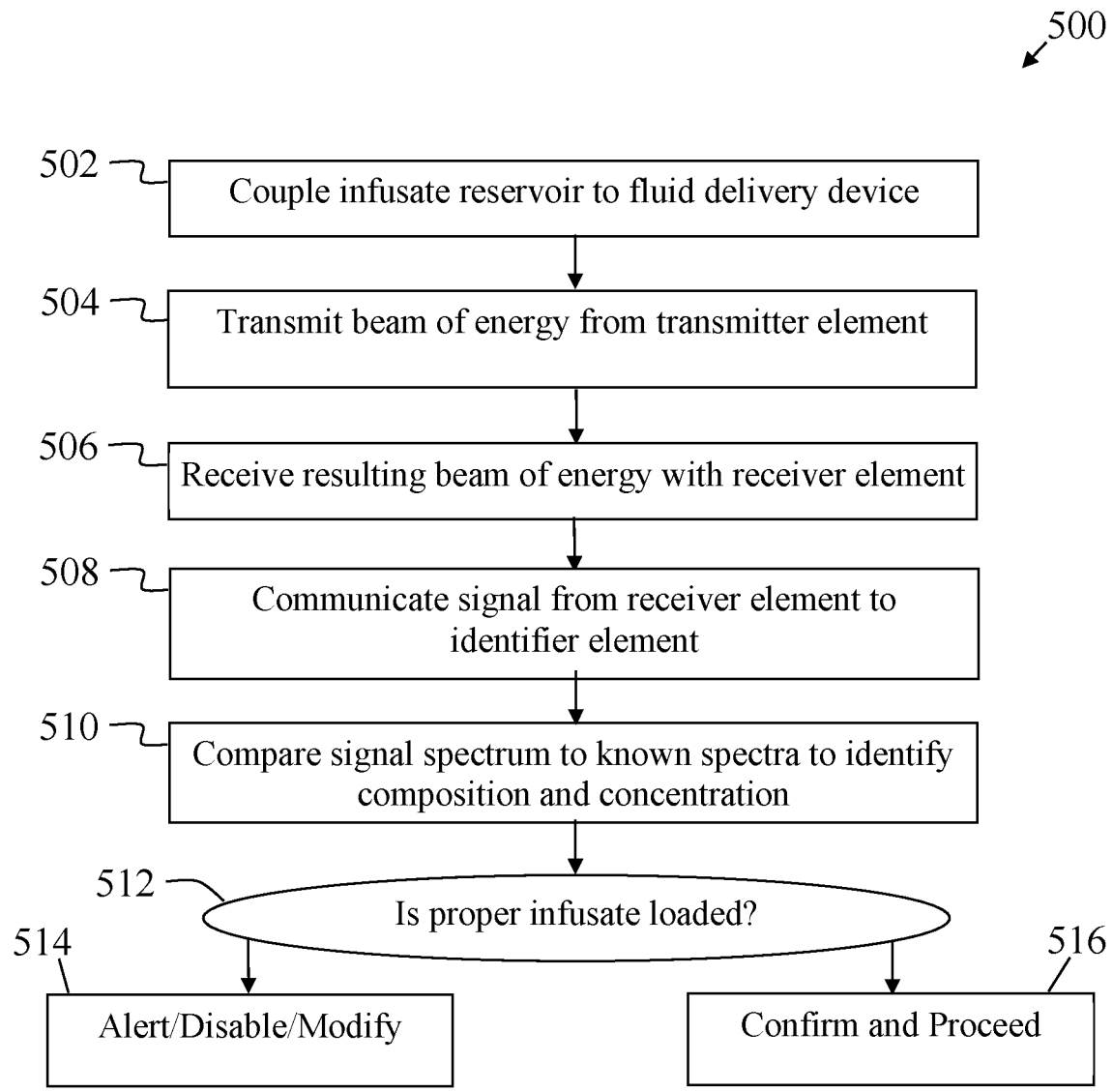
FIG. 7 is a flow chart illustrating an additional method for identifying a fluid for delivery in accordance with an embodiment.

FIG. 7 illustrates an exemplary method 500 for identifying a fluid for delivery to a body of a user. As shown, an infusate reservoir or other container with a conduit holding an infusate is coupled to a fluid delivery device at step 502. Upon coupling, the identification process may be initiated to confirm that the correct infusate is loaded in the fluid delivery device. Alternatively, the identification process may be initiated when fluid is forced out of the reservoir and through a testing location elsewhere in the fluid conduit. For example, at step 504, a beam of energy is transmitted from the transmitter element into the conduit holding the infusate. The beam of energy interacts with the infusate and exits the conduit as a resulting beam of energy. As used herein, a beam of energy reflected at the interface of the conduit and wall bounding the conduit is considered to have passed through the wall and exits the conduit upon reflection with the interface. At step 506, the resulting beam of energy is received by the receiver element.

At step 508, the signal of the resulting beam of energy is communicated from the receiver element to an identifier element. For example, the signal may be wirelessly communicated from the receiver element to the identifier element. The identifier element may be contained within a PCB, sensing arrangement, CCD or computer. The signal is or includes spectroscopic data that may be represented by a spectrum that may be plotted as a graph of energy absorbance (or transmittance) on the vertical axis vs. frequency or wavelength on the horizontal axis.

The identifier element includes or is coupled to a memory storage or library of spectra of known, i.e., previously tested compositions and concentrations. The memory stores data associated with selected fluids for comparison with detected characteristics of the signal. At step 510, the spectrum of the signal is compared to the spectra of known compositions and concentrations. For example, the identifier element may use the stored data to identify the infusate based on the received signal. As is known in absorptive spectroscopic analysis, different compositions and different concentrations of those compositions exhibit unique spectra or signature spectra. For example, differing values of intensity of radiation at specific wavelengths or frequencies or over specific ranges of wavelengths or frequencies may indicate that the beam of energy passed through a specific concentration of a specific composition. Spectral different regions of a reflective NIR/IR spectra graph of fluid-path materials and infusates (insulin formulations) may be used for infusate/bubble tracking. Spectroscopic signals at various wavelengths may be orthogonally used for better identification accuracy.

At step 512, the method queries whether, based on the signal spectrum comparison, the proper or expected infusate is loaded in the fluid delivery device. If not, the PCB, sensing arrangement, CCD or computer may automatically alert the user and/or disable infusion of the infusate from the fluid delivery device at step 514. On the other hand, if the correct infusate is loaded, the PCB, sensing arrangement, CCD or computer may confirm that the correct infusate is loaded and allow the fluid delivery device to proceed with an infusion process at step 516.

While the subject matter is described above primarily in the context of a reservoir containing insulin for regulating a glucose level of a user, the subject matter described herein is not limited to any type of media dispensed from or otherwise provided by the reservoir, and the subject matter may be implemented with other medical devices or electronic devices other than fluid infusion devices. For example, any electronic device could be configured to analyze and identify the composition and concentration of a fluid contained in a reservoir through selective contact with an indicator, image capture of the fluid and indicator, and image analysis.

For the sake of brevity, conventional techniques related to glucose sensing and/or monitoring, closed-loop glucose control, sensor calibration, electrical signals and related processing, electrical interconnects or interfaces, packaging, fluid communications, fluid monitoring or measuring, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not necessarily limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. An apparatus for identifying an infusate in a reservoir of an infusion device, the apparatus comprising:

an enclosed chamber;
a first opening formed between the reservoir and the chamber, wherein the first opening provides a first fluid path out of the reservoir and wherein the first fluid path ends in the chamber;
a valve located in the first opening to provide selective fluid communication between the reservoir and the chamber;
an indicator located in the chamber, wherein the indicator exhibits a visual change when contacted by an infusate;
a detector arrangement to identify the infusate by detecting the visual change in the indicator; and
a second opening in the reservoir to convey the infusate for delivery to a user, wherein the second opening provides a second fluid path out of the reservoir to convey the infusate into a user;
wherein the first fluid path and the second fluid path are non-coincident.

2. The apparatus of claim 1 wherein the indicator exhibits a color change when contacted by the infusate.

3. The apparatus of claim 1 wherein the indicator exhibits a change to a first color when contacted by the infusate at a first concentration or exhibits a change to a second color when contacted by the infusate at a second concentration.

4. The apparatus of claim 1 further comprising a wall enclosing the chamber, wherein at least a portion of the wall is transparent, and wherein the detector arrangement receives light from the chamber through the transparent portion of the wall.

5. The apparatus of claim 1 wherein the detector arrangement comprises:
a camera to capture an image of the infusate and indicator in the chamber and to generate a signal including image data;
a memory storing a library of signals associated with respective infusates; and
an identifier element in communication with the camera to receive a signal including image data and in communication with the memory to compare the signal to the library of signals.

6. The apparatus of claim 1 wherein the valve is a one-way valve interconnecting the reservoir and the chamber, wherein the one-way valve selectively allows fluid flow from the reservoir to the chamber and prohibits fluid flow from the chamber to the reservoir.

7. The apparatus of claim 1 wherein the valve is a capillary tube interconnecting the reservoir and the chamber, wherein the capillary tube selectively allows fluid flow from the reservoir to the chamber and prohibits fluid flow from the chamber to the reservoir.

8. A system for use in filling a fluid delivery device, the system comprising:
a reservoir to hold a fluid and adapted for connection to the fluid delivery device;
a one-way valve interconnecting the reservoir and a chamber, wherein the one-way valve selectively allows fluid flow from the reservoir to the chamber and prohibits fluid flow from the chamber to the reservoir, and wherein the chamber has no exit permitting fluid flow out of the chamber;
a camera to capture an image of the fluid in the chamber and generate a signal including image data; and
an identifier element in electronic communication with the camera to analyze the signal to identify the fluid.

9. The system of claim 8 wherein further comprising a wall enclosing the chamber, wherein at least a portion of the wall is transparent, and wherein the camera receives light from the chamber through the transparent portion of the wall.

10. The system of claim 8 wherein the identifier element is electronically coupled to a memory storing a library of signals associated with respective fluids.

11. The system of claim 8 wherein the one-way valve is a capillary tube interconnecting the reservoir and the chamber.

12. The system of claim 8 further comprising an indicator located in the chamber, wherein the indicator exhibits a visual change when contacted by the fluid.

13. The system of claim 12 wherein the indicator exhibits a color change when contacted by the fluid.

14. The system of claim 8 further comprising
a transmitter element to transmit a beam of energy for interaction with the fluid;
a receiver element to receive a signal from the beam of energy after interaction with the fluid; and
an identifier element coupled to the receiver element to analyze the signal.

15. A method for identifying an infusate in a reservoir of an infusion device, the method comprising:
filling the reservoir with the infusate, wherein a delivery portion of the infusate remains in the reservoir, wherein a test portion of the infusate flows through a one-way valve into a chamber and contacts an indicator located in the chamber, and wherein the indicator exhibits a visual change when contacted by the infusate;
preventing fluid flow of the test portion of the infusate out of the chamber and holding the test portion of the infusate and the indicator in the chamber, wherein the chamber has no exit permitting fluid flow out of the chamber;
capturing an image of the test portion of the infusate and indicator in the chamber;
generating a signal including data associated with the image;
analyzing the signal to identify the infusate; and
delivering the delivery portion of the infusate to a user without passing the delivery portion of the infusate through the chamber.

16. The method of claim 15 wherein analyzing the signal to identify the infusate comprises comparing the signal to previously recorded signals associated with selected infusates.

17. The method of claim 15 wherein the indicator exhibits a color change when contacted by the infusate.

18. The method of claim 15 wherein the indicator exhibits a change to a first color when contacted by the infusate at a first concentration or exhibits a change to a second color when contacted by the infusate at a second concentration.

19. The method of claim 15 wherein the test portion of the infusate remains in the chamber when the delivery portion of the infusate is delivered to a user.

* * * * *